(12) United States Patent
Hsieh et al.

(10) Patent No.: US 12,121,920 B2
(45) Date of Patent: Oct. 22, 2024

(54) MICROSTRUCTURED NOZZLE

(71) Applicant: MICROBASE TECHNOLOGY CORP., Taoyuan (TW)

(72) Inventors: Shu-Pin Hsieh, Taoyuan (TW); Yi-Tong Chen, Taoyuan (TW); Yi-Ting Lin, Taoyuan (TW); Po-Chuan Chen, Taoyuan (TW)

(73) Assignee: MICROBASE TECHNOLOGY CORP., Taoyuan (TW)

( * ) Notice: Subject to any disclaimer, the term of this patent is extended or adjusted under 35 U.S.C. 154(b) by 1105 days.

(21) Appl. No.: 16/343,404

(22) PCT Filed: Nov. 6, 2017

(86) PCT No.: PCT/CN2017/109589
§ 371 (c)(1),
(2) Date: Apr. 19, 2019

(87) PCT Pub. No.: WO2018/082699
PCT Pub. Date: May 11, 2018

(65) Prior Publication Data
US 2019/0240427 A1    Aug. 8, 2019

Related U.S. Application Data

(60) Provisional application No. 62/418,195, filed on Nov. 6, 2016, provisional application No. 62/418,174, filed on Nov. 6, 2016.

(51) Int. Cl.
*B05B 1/02* (2006.01)
*A61M 11/00* (2006.01)
(Continued)

(52) U.S. Cl.
CPC ......... *B05B 11/109* (2023.01); *A61M 11/003* (2014.02); *A61M 15/0065* (2013.01);
(Continued)

(58) Field of Classification Search
CPC .................................................. A61M 11/003
See application file for complete search history.

(56) References Cited

U.S. PATENT DOCUMENTS

2005/0001076 A1*  1/2005  Eicher .................... A61M 11/06
                                                        239/590.5
2007/0210029 A1   9/2007  Spitz et al.

FOREIGN PATENT DOCUMENTS

CN    1087843 A    6/1994
CN    1271296 A   10/2000
(Continued)

OTHER PUBLICATIONS

The internationl search report and the written opinion of the International Search Authority, Jan. 31, 2018, whole document, SIPO as ISA.
(Continued)

*Primary Examiner* — Jason J Boeckmann
(74) *Attorney, Agent, or Firm* — OPES IP Consulting Co. Ltd.

(57) ABSTRACT

A microstructured passage module for aerosolizer is disclosed. The module includes a plate overlaid by a cover, an entrance, an exit, a plurality of protrusions and a plurality of pillars. The protrusions and pillars project from and are integral parts of the plate. Further, the plate can be divided into a first zone proximate to the entrance and a second zone proximate to the exit. The protrusions are arranged into parallel rows in a direction from the entrance to the exit and form parallel passages therebetween in the first zone for the liquid to flow along. The protrusions in each column are spaced from one another by tunnels. The pillars are interposingly disposed in the second zone and define certain channels therebetween. Moreover, a plurality of pillars fur-
(Continued)

ther disposed in the passages increase a flow resistance for the liquid flowing through the passages.

17 Claims, 4 Drawing Sheets

(51) Int. Cl.
*A61M 15/00* (2006.01)
*A61M 31/00* (2006.01)
*B05B 1/10* (2006.01)
*B05B 1/26* (2006.01)
*B05B 1/34* (2006.01)
*B05B 11/10* (2023.01)
*B05B 11/00* (2023.01)

(52) U.S. Cl.
CPC .......... *A61M 15/009* (2013.01); *A61M 31/00* (2013.01); *B05B 1/02* (2013.01); *B05B 1/10* (2013.01); *B05B 1/26* (2013.01); *B05B 1/34* (2013.01); *B05B 11/1074* (2023.01); *A61M 11/007* (2014.02); *A61M 2205/0216* (2013.01); *A61M 2205/0222* (2013.01); *A61M 2205/0238* (2013.01); *A61M 2205/121* (2013.01); *A61M 2207/00* (2013.01); *A61M 2210/0625* (2013.01); *B05B 11/0038* (2018.08)

(56) References Cited

FOREIGN PATENT DOCUMENTS

| | | |
|---|---|---|
| CN | 1809424 A | 7/2006 |
| CN | 100496759 C | 6/2009 |
| EP | 1493492 A1 | 1/2005 |
| WO | WO2005014175 A1 | 2/2005 |

OTHER PUBLICATIONS

Office Action Communication from TIPO, Jan. 31, 2019.
Extended European search report by the EPO, Oct. 22, 2019.
Office action by CNIPO, Jul. 14, 2020.

* cited by examiner

MICROSTRUCTURED NOZZLE

CROSS REFERENCE TO RELATED APPLICATION

The present application claims priority to PCT Application PCT/CN2017/109589 filed on Nov. 6, 2017, which claims priority to U.S. Provisional Application Ser. No. 62/418,174 filed on Nov. 6, 2016 and U.S. Provisional Application Ser. No. 62/418,195 filed on Nov. 6, 2016, which are both incorporated by reference in their entirety.

FIELD

The present disclosure relates to a microstructured passage module and more particularly to a microstructured passage module for an aerosol generator.

BACKGROUND

Aerosolizer, also known as nebulizer or atomizer, is used to deliver medication to patients for inhalation. Particularly, liquid medicament is broken down into aerosol having fine particles/droplets for easier and more efficient inhalation and absorption. The particle size may be adjusted depending on different respiratory conditions, such as Chronic Obstructive Pulmonary Disease (COPD) or asthma, or depending on the requirement of the liquid medicament itself. Receiving the same precise amount of medication in each treatment is also very important for patients. In other words, a good aerosolizer should be able to deliver a precise dosage of medication having a fixed average particle size in every respective operation to reduce waste and risks of overdosing.

Referring to FIG. 1, an exemplary aerosolizer includes an upper casing, a lower casing, a nozzle assembly, a tube, a biasing element and a storage container. During preparation, the biasing element, such as a spring, is tensioned by the relative movement of the upper casing and the lower casing. Meanwhile, a fixed amount liquid medicament is drawn from the storage container by the tube and to the nozzle assembly, ready to be aerosolized. When the aerosolizer is actuated, a force generated by the un-tensioned biasing element pushes the fixed amount of liquid medicament towards and through the nozzle assembly, thereby creating the aerosol for inhalation. Another exemplary aerosolizer and the operation mechanism thereof can be referenced to the disclosure in U.S. Pat. No. 5,964,416 (U.S. patent application Ser. No. 08/726,219).

As shown in FIG. 1, pressurized liquid medicament travels in the direction from A to A', i.e., from a high pressure point to a low pressure point. Liquid medicament is drawn and forced into the nozzle assembly, through which aerosol is generated and exited out. During aerosolization, it is crucial that proper seal is maintained between the components inside the aerosolizer. Otherwise, the resulting aerosolization effect may be compromised. For example, a leak at the nozzle assembly may lead to pressure loss, which can result in delivery of unprecise dosage or inappropriate aerosol particle size. To achieve proper seal, components of the aerosolizer must be manufactured and assembled with caution and precision. However, due to the miniature size of the components, usually in the scale of millimeters or less, achieving proper seal tends to be difficult and costly. Moreover, miniature components of different geometric shapes may be more prone to wear and tear in a high-pressure (usually between 5 and 50 MPa, which is about 50 to 500 bar) environment.

In another aspect, the nozzle assembly plays a vital role in whether the pressurized liquid medicament can be aerosolized into fine particles/droplets and leave the aerosolizer at a certain speed. As shown in FIG. 1, the pressurized liquid medicament travels through the central connecting tube to the nozzle assembly and through the nozzle. The pressurized liquid medicament flows into the nozzle at a high speed. The nozzle serves to filter and decrease the flow speed of the liquid medicament in a controlled manner such that precise dosage can be aerosolized into the desired aerosol form. The foregoing may be achieved through specifically designed internal structure of the nozzle. Improper design of the nozzle may lead to blockage to the entire aerosolization process, which may shorten the life of the aerosolizer or affect dosage accuracy.

A typical nozzle used in an aerosolizer includes multiple elements with different geometric shapes. For example, some elements with a particular shape, e.g., elongated projections, are used as filters. Some other elements with a different shape, e.g., cylindrical projections, are used to structure a guiding system to control the liquid flow in the nozzle. In short, a nozzle used in the relevant art requires the combination and interaction of multiple elements having different structural and/or functional characteristics in order to achieve the desired aerosolization effect. However, due to the miniature size of the nozzle, fluid control therein is not easy. The structure, dimension and arrangement of the elements in the nozzle need to be carefully designed and implemented to make the nozzle effective. As a result, the costs for the design and manufacture of the nozzle tend to be high.

The present disclosure aims to provide a nozzle structure with elements of less complicated structure, design and arrangement. The resulting nozzle will improve the overall aerosolization quality and efficiency, while the cost for manufacturing such nozzle is lowered. Accordingly, patients can enjoy a more cost-effective treatment solution.

SUMMARY

The present disclosure provides a microstructured passage module for an aerosol generator. The passage module is formed by a plate overlaid by a cover.

The plate can be divided into a first zone and a second zone. A liquid flow direction, which is perpendicular to the side of the entrance, is defined. The first zone of the plate includes an entrance for liquid to enter. The first zone also includes a plurality of protrusions arranged in rows in the liquid flow direction, and in columns over the entire width of the first zone defining a plurality of passages therebetween. The plurality of protrusions are elongated shaped and are substantially parallel to each other. Furthermore, the plurality of passages in between columns of protrusions are arranged to correspond to the liquid flow direction, and each rows of protrusion is spaced by a tunnel. The second zone includes a plurality of pillars. At least section of the passages in the first zone also include pillars. The plurality of pillars defines a plurality of channels inbetween for liquid medicament to flow. These plurality of pillars in the passages increase the flow resistance of the liquid travelling through the passages. The plurality of protrusions and pillars project from and are integral parts of the plate.

In some embodiments, the liquid flows through the plurality of passages via the tunnels.

In some embodiments, the tunnel's length is greater than its width. And the tunnel's length can equal to either the protrusion's length or width.

In some embodiments, the tunnels have different widths.

In some embodiments, the tunnels have the same width.

In some embodiments, the space between the pillar and the protrusion in the first zone is also part of the channel.

In some embodiments, the plurality of pillars are arranged in a matrix fashion.

In some embodiments, the plurality of pillars are arranged in a hexagonal shape.

In some embodiments, the density of the plurality of pillars in the second zone is greater than that in the passages.

In some embodiments, the spray velocity is between 167 to 170 m/s.

In some embodiments, the ratio between the total surface area that the plurality of pillars occupied in the passages to the total surface area of the passages is between 5 to 6%.

In some embodiments, the ratio between the total surface area that the plurality of pillars occupied in the passages to the total surface area of the passages is about 5.5%.

In some embodiments, the shortest distance between any two adjacent pillars is greater than 1 um.

In some embodiments, the plate comprises two sidewalls in the second zone inclining towards the exit.

In some embodiments, the plurality of pillars are further adapted to adjust the liquid's flow speed.

In some embodiments, the columns of the protrusions are parallel.

In some embodiments, the rows of the protrusions are parallel and arranged linearly in the direction of the liquid flow direction.

In some embodiments, the shortest distance between two adjacent pillars in the second zone is at least 8 um.

The present disclosure further provides a microstructured passage module for an aerosol generator. The passage module is formed by a plate overlaid by a cover. The plate can be divided into a first zone and a second zone. A liquid flow direction, which is perpendicular to the side of the entrance, is defined. The first zone of the plate includes an entrance for liquid to enter. The first zone also includes a plurality of walls arranged in column over the entire width of the first zone defining a plurality of passages therebetween. Further, the plurality of passages correspond to the liquid flow direction. The second zone includes a plurality of pillars. At least section of the passages in the first zone also include pillars. The plurality of pillars defines a plurality of channels inbetween for liquid medicament to flow. The ratio between the total surface area occupied by the pillars in the passages to the total surface area of the passages is between 5 to 6%. The plurality of pillars are further adapted to adjust the liquid's flow speed. The plurality of protrusions and pillars project from and are integral parts of the plate.

In some further embodiments, the ratio between the total surface area occupied by the pillars in the passages to the total surface area of the passages is about 5.5%.

BRIEF DESCRIPTION OF THE DRAWINGS

One or more embodiments are illustrated by way of example, and not by limitation, in the figures of the accompanying drawings, wherein elements are having the same reference numeral designations represent like elements throughout. The drawings are not to scale, unless otherwise disclosed.

Figure 1:
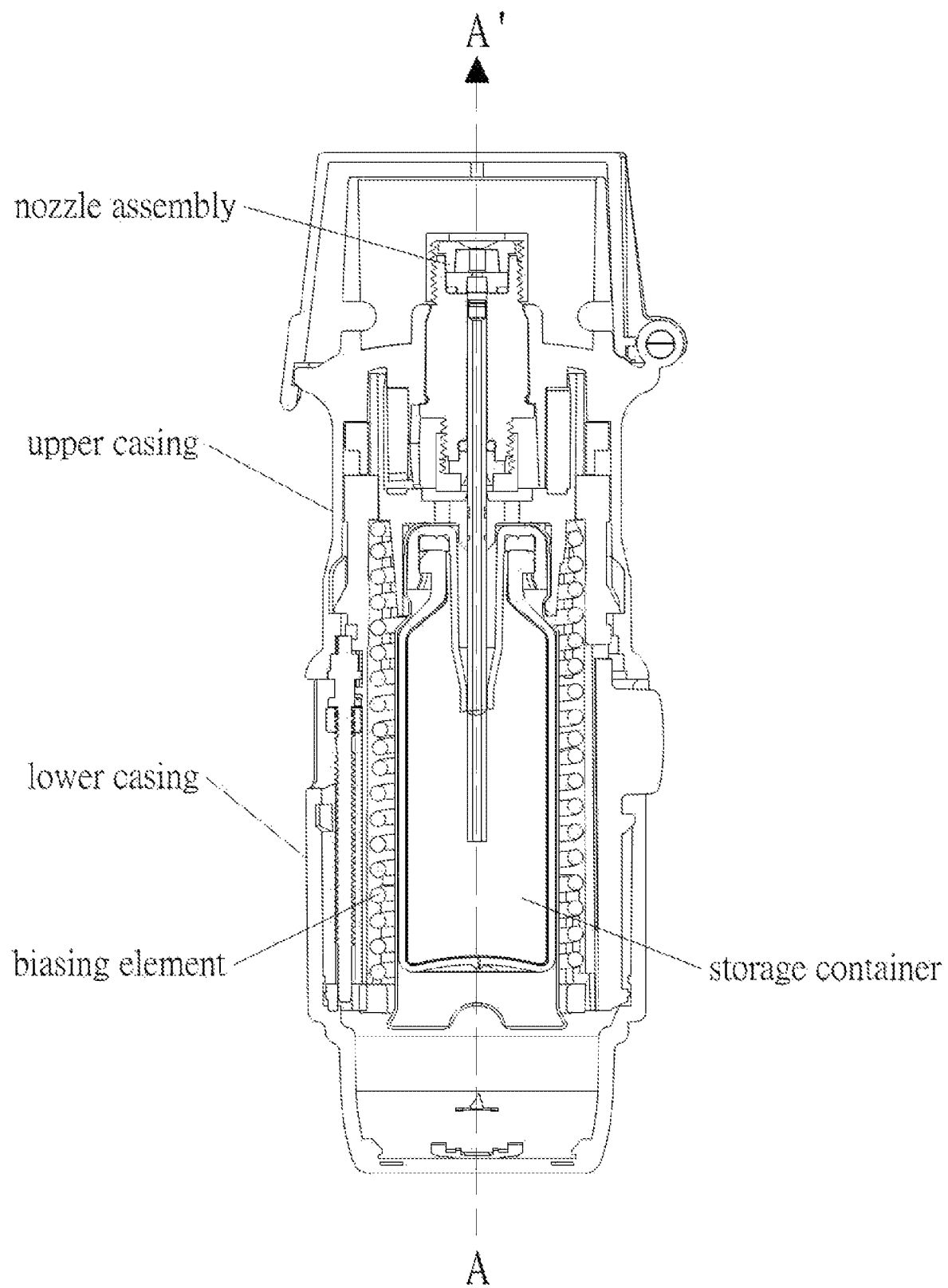
FIG. 1 is a cross section view of an exemplary aerosolizer according to the prior art.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention. Any reference signs in the claims shall not be construed as limiting the scope. Like reference symbols in the various drawings indicate like elements.

DETAILED DESCRIPTION OF THE DISCLOSURE

The making and using of the embodiments of the disclosure are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Throughout the various views and illustrative embodiments, like reference numerals are used to designate like elements. Reference will now be made in detail to exemplary embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, an apparatus in accordance with the present disclosure. It is to be understood that elements not specifically shown or described may take various forms. Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. It should be appreciated that the following figures are not drawn to scale; rather, these figures are merely intended for illustration.

In the drawings, like reference numbers are used to designate like or similar elements throughout the various views, and illustrative embodiments of the present disclosure are shown and described. The figures are not necessarily drawn to scale, and in some instances the drawings have been exaggerated and/or simplified in places for illustrative purposes. One of ordinary skill in the art will appreciate the many possible applications and variations of the present disclosure based on the following illustrative embodiments of the present disclosure.

Definition

It will be understood that when an element is referred to as being "on" another element, it can be directly on the other element or intervening elements may be present. In contrast, when an element is referred to as being "directly on" another element, there are no intervening elements present.

It will be understood that singular forms "a", "an" and "the" are intended to include the plural forms as well, unless the context clearly indicates otherwise. Furthermore, relative terms, such as "bottom" and "top," may be used herein to describe one element's relationship to other elements as illustrated in the Figures.

It will be understood that elements described as "under" or "below" other elements would then be oriented "over" or "above" the other elements. The exemplary terms "under" or "below" can, therefore, encompass both an orientation of over and under.

The term "unsymmetrical," as used herein, refers to a shape of the cross-section of the compartment cannot be capable of division by a longitudinal plane into similar halves. Therefore, according to the previous definitions, the scope of the unsymmetrical shape includes the shape excluded the circle, oval, and equilateral polygon.

The term "width," as used herein such as "a width of the tunnel" and "a width of the passage", refers to a shorter distance between the sides of a pathway (e.g., tunnel and passage) relative to the length.

The term "about," as used herein, when referring to a measurable value such as an amount, a temporal duration, and the like, is meant to encompass variations of ±10% and more preferably ±5% from the specified value, as such variations are appropriate to perform the disclosed methods.

Unless otherwise defined, all terms (including technical and scientific terms) used herein have the same meaning as commonly understood by one of ordinary skill in the art to which this disclosure belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

DETAILED DESCRIPTION

Figure 2:
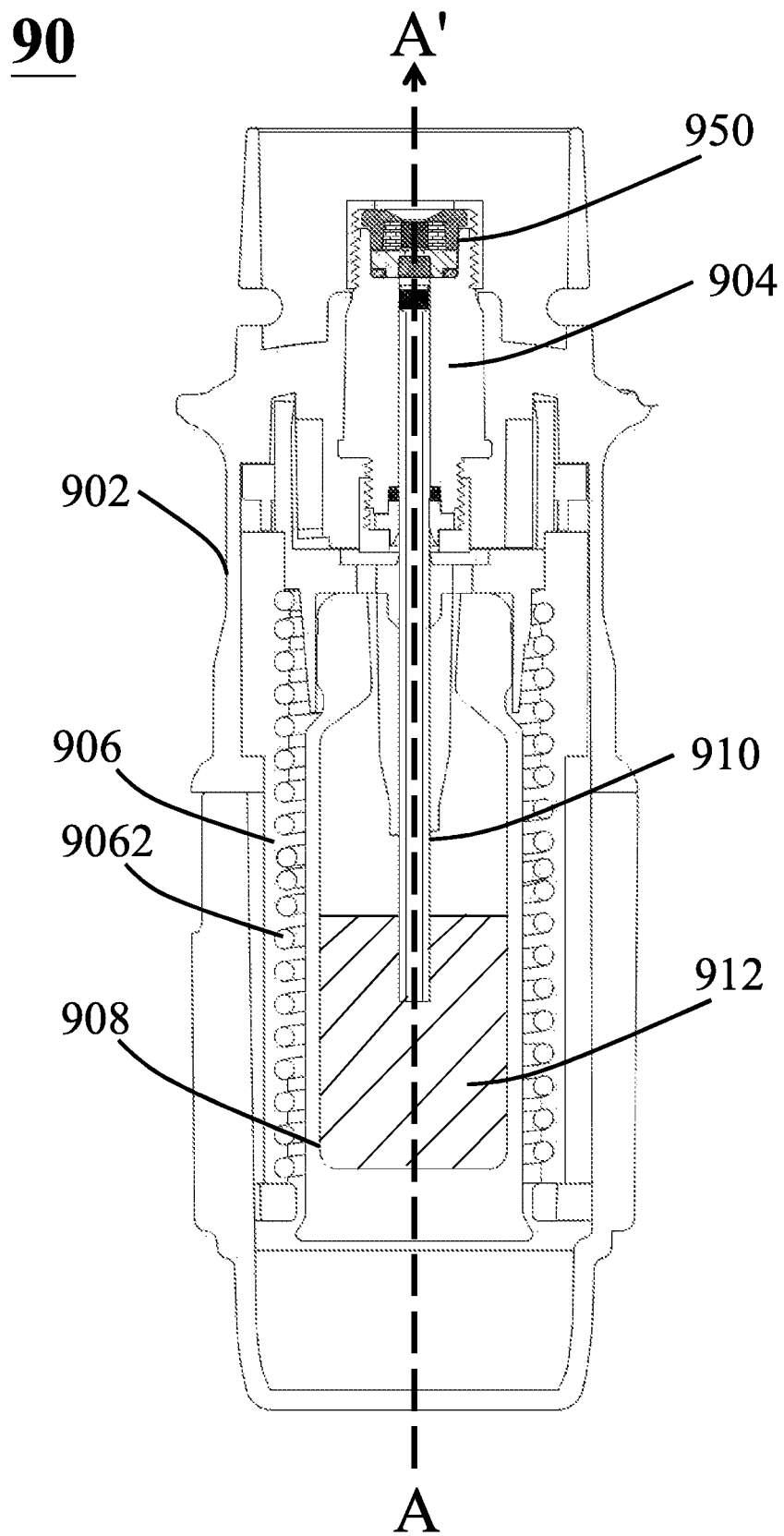
FIG. 2 is a cross section view of another exemplary aerosolizer according to the present disclosure.

FIG. 2 is a cross-sectional view of an exemplary aerosolizer according to the present disclosure. Here, the aerosolizer 90 includes a housing 902 with a pump chamber 904 and a spring chamber 906. A biasing element 9062, such as a spring, is coupled to the housing 902, and more particularly is mounted in the spring chamber 906. The spring chamber 906 also holds a storage container 908 where liquid medicament 912 is stored. Such liquid medicament 912 can be drawn from the storage container 908 via a tube 904 in response to a pre-actuation of the aerosolizer 90. Particularly, prior to actuation, the housing 902 is rotated. The spring 9062 is adapted to respond to such rotation by tensioning. Correspondingly, the liquid medicament 912 is drawn from the storage container 908 into the pump chamber 904, ready to be aerosolized. The aerosolization process starts when the aerosolizer 90 is actuated. When actuated, a release mechanism (not shown) is triggered and the spring 9062 is released from the tensioned state to the untensioned state. Such operation results in a force pushing the liquid medicament 912 through a transfusion apparatus 950, where a microstructured passage module 1 (i.e., nozzle) resides, at the pump chamber 904. In other words, the liquid medicament passes through the microstructured passage module 1 for aerosolization. The microstructured passage module 1 is specifically designed such that aerosol having desired particle size in a controlled and precise delivery manner can be produced. Consequently, aerosolized liquid medicament, such as aqueous solution or ethanoic solution, exits the transfusion apparatus 950 and then out of the aerosolizer 90 for patient inhalation.

The microstructured passage module 1 is the crucial component of the aerosolizer 90 where liquid medicament can be broken down into aerosol having fine particles/droplet. The microstructured passage module 1 of the aerosolizer 90 is a component having a microstructured filtering and guiding system, which consists of a plurality of microscale elements and a plurality of passages defined by the microscale elements. When the liquid medicament travels into the microstructured passage module 1 at a high speed, the microscale elements will partially block the flowing medicament and parse it into small particles. Furthermore, the configuration of the microscale elements and the passages will increase flow resistance, thereby reduce the liquid flow speed. However, the flow speed of liquid medicament instantly increases due to the funnel-shaped outlet of the microstructured passage module 1 when the liquid medicament exits the outlet, and therefore an amount of the filtered liquid medicament having a particular size particle is aerosolized and sprayed FIGS. 3A-3D are of cross-section views of the microstructured nozzle in accordance with some embodiments of the present disclosure.

Figure 3A:
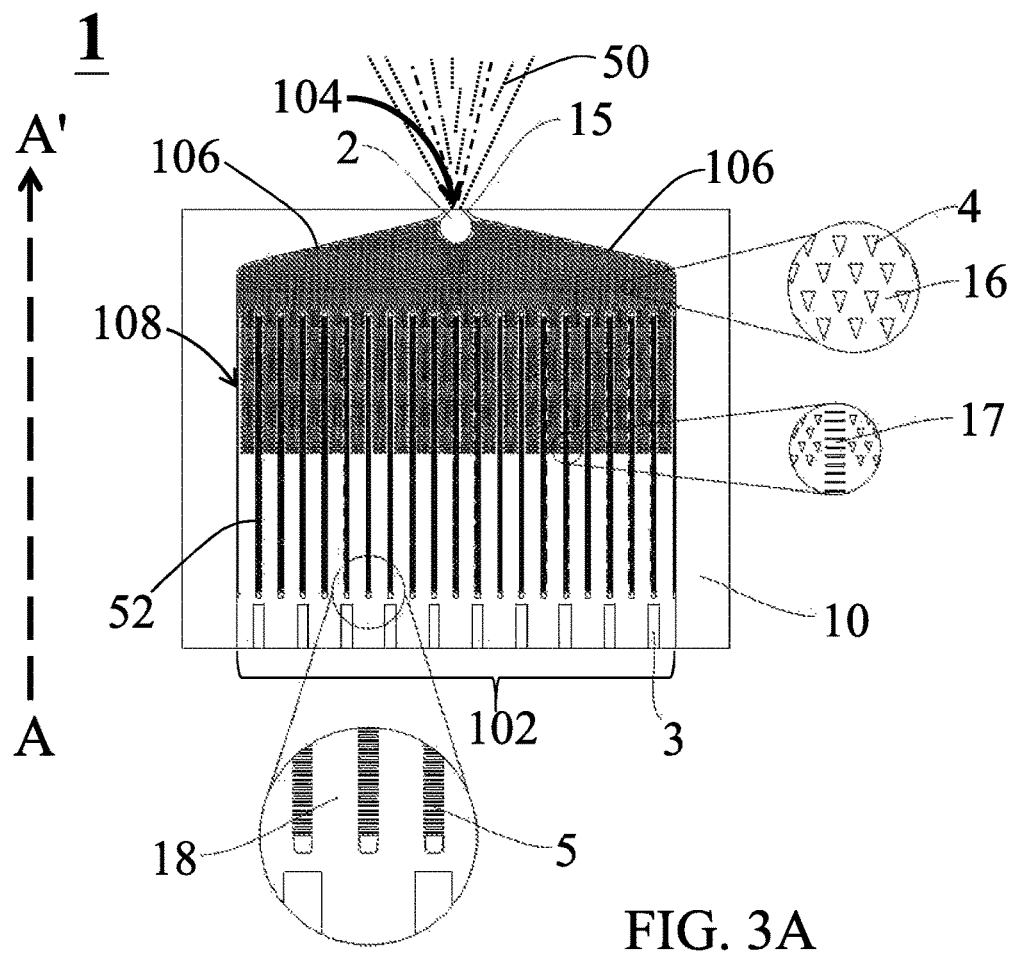
FIGS. 3A-3D are cross-section views of the microstructured passage module in accordance with some embodiments of the present disclosure.

Referring to FIG. 3A, a microstructured passage module 1 is disclosed. The microstructured passage module 1 includes a plate 10, which can be made from silicon and is about 2.5 mm in width, about 2 mm in length and about 700 um in depth. The plate 10 is overlaid by a glass cover (not shown), which is about 2.5 mm in width, about 2 mm in length and about 625 um in depth, thus defining a compartment. Liquid medicament (not shown) enters the compartment via the entrance 102 at one end. The resulting aerosol 50 leaves the compartment via the exit 104 at the opposite end. The entrance 102 has a width about 2 mm, which is wider that the exit 104. Liquid medicament in the compartment flows along in the general direction from the entrance 102 to the exit 104. A flow direction of the liquid medicament in the passage module 1, which is perpendicular to the side of the entrance 102, is defined by the direction from A to A'. At least some of the liquid medicament will flow along the inclined walls 106 of the passage module 1, causing liquid flows to collide against each other, preferably at about 90°. As a result, aerosol 50 is created for patient inhalation.

The plate 10 generally can be divided into two sections by the boundary line B, which are a first zone proximate to the entrance 102 and a second zone proximate to the exit 104. The plate 10 also includes several components, such as a central block 2, spacers 3, pillars 4 and protrusions 5. Particularly, protrusions 5, pillars 4 and spacers 3 are disposed in the first zone, while the second zone only includes pillars 4. Protrusions 5, pillars 4, spacers 3 and central block 2 are adapted to project from the plate 10 in the direction transversely to the liquid flow direction. In one option, these components may be formed as integral parts of the plate 10 by etching the microstructured passage module 1. In certain embodiments, a depth of about 5-6 um of the plate 10 is etched so as to form such integral components. Note that the manufacturing method of the plate 10 is not so limited. The plate 10 may be manufactured by other means known in the relevant art, such as molding, welding or printing. Further characteristic and the configuration of the integral components are further described below.

Still in FIG. 3A, a central block 2 is disposed proximate to the exit 104 and in the second zone. The central block 2 is sphere-like, having a radius of curvature about 37.35 um. The central block 2 obstructs a substantial part of the compartment proximate to the exit 104 to the extent that the liquid may only flow to the exit 104 by bypassing via two aisles 15 between the central block 2 and the inclined walls 106. The foregoing configuration directs liquid into opposite flows against each other, i.e., along two opposite aisles 15. In other words, the microstructured passage module 1 can be understood to include two exits for the purpose of desired aerosolization. As a result, opposite liquid jets exiting the microstructured passage module 1 collide into each other at a location external to the passage module 1 but proximate to the exit 104, forming the aerosol 50. The central block 2 is dimensioned such that each aisle 15 is about 8 um in width and 53.8 um in length. Moreover, the total area of each aisle 15 is about 44 um$^2$.

A plurality of spacers 3 about 50 um wide and 200 um long are disposed near the entrance 102 and in the first zone. The spacer 3 has elongated shape, orientation of which aligns with the liquid flow direction A to A'. Further, the spacers 3 may be arranged in multiple columns over an entire width of the entrance 102 of the first zone. As depicted, a plurality of protrusions 5 are arranged in parallel columns 52 across the entire width of the first zone. These parallel columns 52, made of linear rows of protrusions 5, are located in the first zone. Between each parallel columns 52 is a passage 18 for the liquid medicament to flow. The liquid flow via the plurality of passages in the direction A to A'. The dimension of such passage is about 77 um wide and 1.3 mm long. Column 52 may have a general dimension of about 22 um wide and 1.3 mm long. The column 52 may be arranged to be parallel to the liquid flow direction A to A'. Since passage 18 is defined as the area between two parallel columns 52, the length for the column 52 and the passage is the same.

The distance between two adjacent spacers 3 is about 150 um, which is approximately two times the width of the passage 18. For the unfiltered liquid medicament entering the microstructured passage module 1, the space between two spacers 3 are used as preliminary filters, and the space between two columns 52 are used as secondary filters. For example, any particle size larger than 150 um will be first filtered by the space between two spacers 3; and any particle size larger than 8 um will be subsequently filtered by the space between two adjacent triangle pillars in the passages. Further, the filtering function will not affect the liquid flow direction because the channels will not be completely blocked by the particles.

As FIG. 3A shows, the protrusion 5 is an elongated element, about 2.5 um in width and 22 um in length. In a preferred embodiment, the protrusion 5 is positioned in an orientation where the width of the protrusion 5 is parallel to the liquid flow direction A to A'. However, the orientation of the protrusion 5 is not limiting. In each column 52, the plurality of protrusions 5 are further arranged in rows, in a linear arrangement in the direction of A to A'. In one embodiment, the rows may be parallel to each other.

Figure 3B:
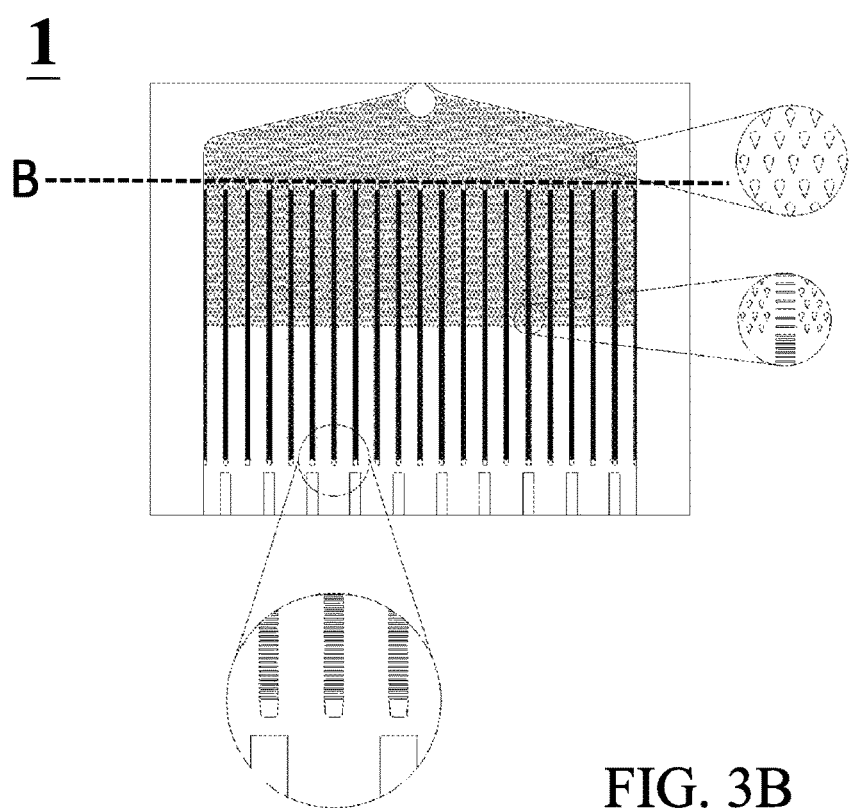
Figure 3C:
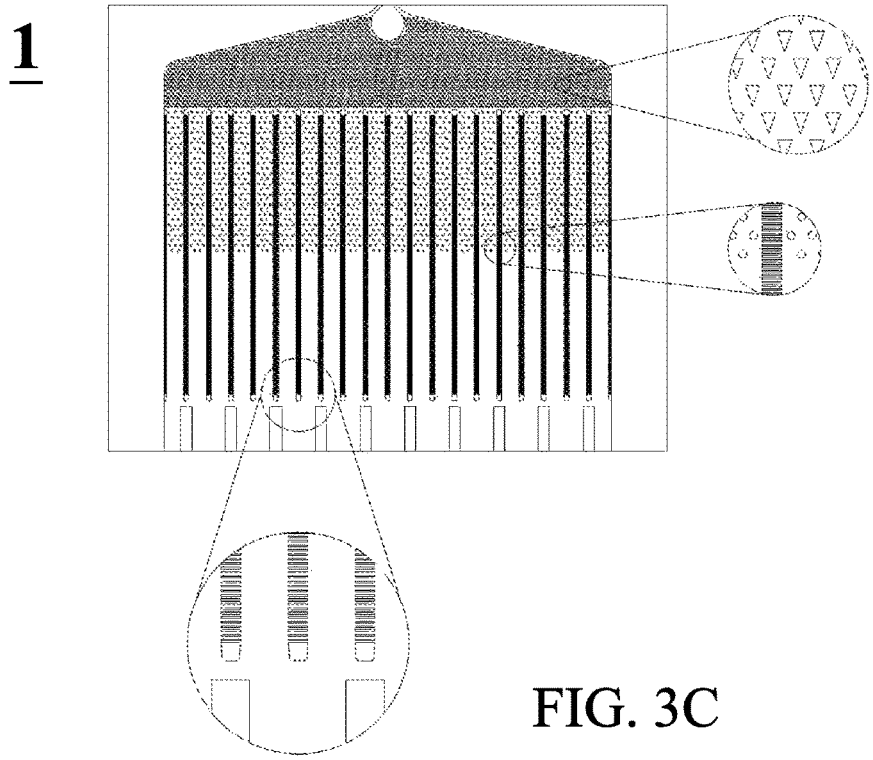

Each row of the linear protrusions 5 is spaced by a tunnels 17. The width of each tunnel may or may not be same, depending on the requirement of the aerosolizer or medicament. In one embodiment, the width of each tunnel 17 is the same, as depicted in FIG. 3C. The dimension of the tunnel 17 is about 3 um in width and 22 um in length. In other embodiments, the tunnels 17 include at least two different widths, each about 3 um and 11 um, as depicted in FIGS. 3A and 3B. In a preferred embodiment, however, the width of the tunnel must be ≥1 um.

The directions of the tunnels 17 and passages 18 are not parallel to each other. In the present disclosure, the tunnels 17 and the passages 18 are perpendicular to each other. Liquid medicament may flow between the passages 18 through the tunnels 17.

In certain embodiments, the length of each protrusion 5 is equal to the length of each tunnel 17, which is greater than the width of the tunnel 17. In another embodiment, the width of each protrusions 5 is equal to the length of each tunnel 17, which is still greater than the width of tunnel 17. It is to be noted that although the figures herein show that there are columns 52 arranged in contact with the inner sidewalls 108, it is not meant to be limiting. For example, the sidewalls 108 may be a standalone element, i.e., not in contact with any of the integral components.

Figure 3D:
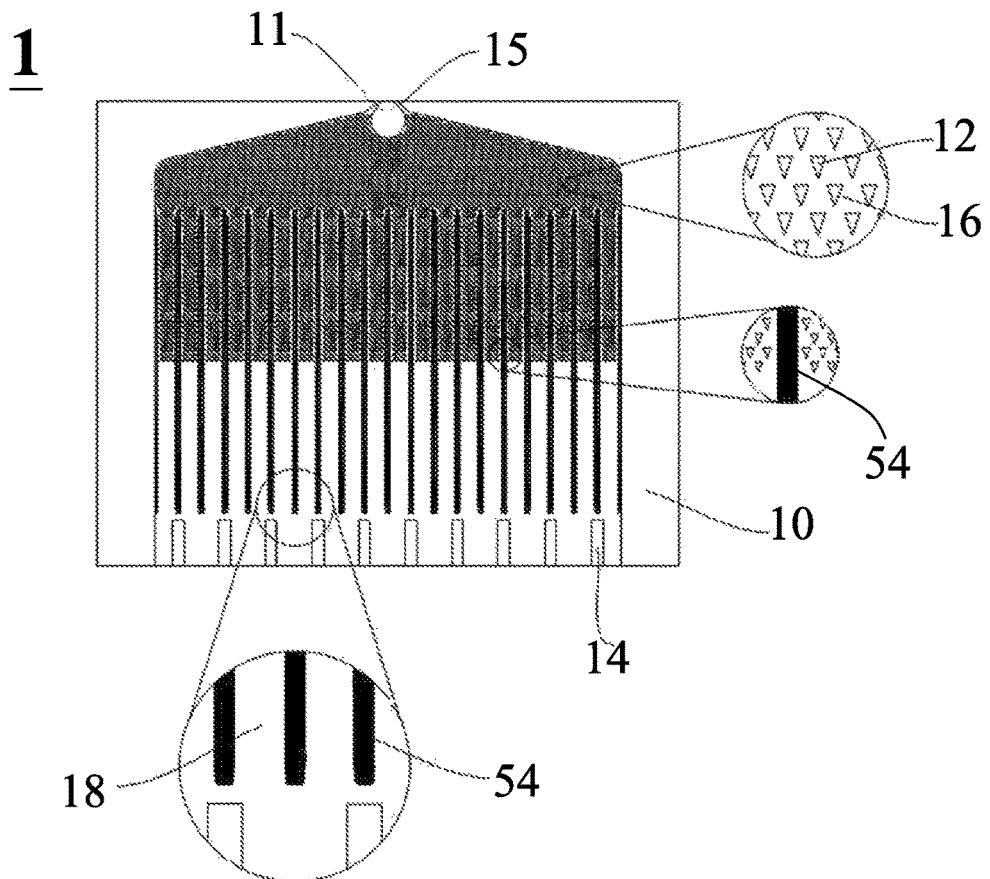

The present disclosure further provides another microstructured passage module 1 configured to include no tunnel 17. That is, the column 52 is made of one solid, continuous protrusion or wall 54, as FIG. 3D shows. The design and arrangement of such wall 54 is similar to that of the column 52 except the wall 54 is not made of individual rows of protrusions 5 separated by tunnels 17. The wall 54 is one solid structure that extends in the direction A to A' in the first zone. Absent any tunnel, liquid medicament in passages 18 may not communicate with each other. Each wall 54 is about 22 um in width and 1.3 mm in length.

With reference to FIGS. 3A to 3D, the microstructured passage module 1 further includes a plurality of pillars 4. The pillars 4 are located in the second zone, i.e., close to the exit 104. In some embodiments, the pillars 4 also extend into the first zone, occupying certain sections of the passages 18. In yet some other embodiments, the pillars 4 may be distributed in all areas of the passages 18. The pillars 4 are microscaled elements that project from the plate 10 with a height of about 5-6 um.

The pillars 4 may be of any geometric shape suitable for providing filtering function. In some embodiments, the pillar 4 includes at least three sidewalls and the cross-section of the pillar 4, in the direction parallel to the plate, can be unsymmetrical or symmetrical. Furthermore, such cross-section of the pillar 4 includes at least one vertex facing the entrance 102 having an angle formed by its intersecting walls to be less than 90°. Therefore, the cross-section of the pillar 4 may be circular, triangular, diamond-like and so on. In some embodiments of the present disclosure, the cross-section of pillar 4 is a triangle having sidewalls about 8 um long and a vertex that is facing the entrance 102. The angle formed by the two walls of the vertex facing the entrance is about 60°. In some embodiments, the cross-section of the pillar 4 may be an equilateral, isosceles or scalene triangle.

In another embodiment of the present disclosure, the cross-section of the pillar 4 is a droplet having its sphere end facing the outlet 104, as FIG. 3B shows. In yet other embodiments, the cross-section of the pillar 4 is a circle having a diameter about 10 um. The plurality of pillars 4 in the microstructured passage module 1 may all have the same shape and dimension. However, with reference to FIG. 3C, in certain embodiments, the pillars 4 may have different shapes and dimensions. For example, the pillars 4 in the second zone may have a different shape and dimension than those in the first zone. Moreover, the density of the pillars 4 in the first and second zones may also be different.

In another aspect, the pillars 4 may be arranged in a matrix-like fashion to at least partially obstruct the flow of the liquid, hence increasing flow resistance and decreasing the flow speed. In a preferred embodiment, the pillars 4 are arranged in a hexagonal shape. Specifically, the hexagonal design includes one center pillar and six adjacent pillars forming the six vertices of the hexagonal shape. Such arrangement may provide appropriate flow resistance for the liquid, while reduce the possibility of total liquid blockage.

In certain embodiments, spaces/pathways inbetween the plurality of pillars 4 are defined as channels 16. Such channels 16 also include the spaces/pathways between the pillar 4 and the adjacent protrusion 5 in the first zone. In one preferred embodiment, the shortest distance between any two adjacent pillars is adapted to be greater than the width of any tunnel.

Attention is now directed to certain arrangement of the pillars 4, and more particularly the density thereof, in the present disclosure. Here, a ratio between the total surface area that the pillars 4 occupy in a certain space to the total surface area of such certain space is defined as the pillar density. The pillar density of the second zone is preferably to be about 13.9%.

Particularly, the pillar density in the passages is defined as the ratio between the total surface areas occupied by the pillars 4 in the passages to the total surface area of the passages. Another, the pillar density in the second zone is the ratio between the total surface areas that the pillars 4 occupy in the second zone to the total surface area of the second zone. In one embodiment, the pillar density in the passages 18 is less than the pillar density in the second zone since only sections of the passages 18 contain pillars 4. The pillar density in the passages 18 should be between 5 to 6%, and preferably about 5.5%.

Due to the difference in pillar density, flow resistance will increase when liquid enters the second zone from the first zone. The aerosolizer of the present disclosure is capable of delivering aerosol 50 having an effective spray duration of about 1.4 to 1.5 seconds, which is desired because the aerosol speed is relatively low. Lower aerosol speed results in better and more controlled delivery of aerosol as it reduces residue built up in the patient's mouth and throat. Conversely, if aerosol speed is too high, the desired inhalation effect may not be achieved. For example, the aerosol 50 may travel too fast for the patient to inhale properly and completely, or the aerosol 50 may be blocked by the patient's mouth/throat. It is to be noted that the speed and spray duration of the aerosol 50 can be measured by different methods such as video recording or laser light diffraction. Different measurement methods may result in different outcomes.

Attention is now directed to the arrangement and configuration of the pillars 4 and tunnels 17. The pillars 4 serve to (i) adjust/guide the direction of the liquid medicament flow, (ii) change the flow resistance and flow speed for the liquid medicament; and (iii) filter the liquid medicament into smaller particles, such that the quality of aerosol will not be affected. The adjustment of flow direction by pillars 4 results in liquid flowing through different channels 16. The increasing flow resistance and decreasing flow speed may result in turbulence around the pillars 4 when at least part of the liquid flow collides with pillars 4. Tunnels 17 allows small amounts of liquid medicament to flow traversely across the passages 18, thereby also reducing the overall flow speed of the medicament. The present disclosure provides several designs of the pillars 4 and their effects as shown in Table 1 below.

TABLE 1

| No. | Width of Channel First Zone (um)/ Pillar Shape in passage | Total Surface Area Occupied by Pillars in the Passages (m$^2$) | Pillar Density (Passages) | Width of Channel Zone2/pillar shape (um) | Pillar Density (second zone) | Spray Velocity (m/s) |
|---|---|---|---|---|---|---|
| 1 | 8/triangle | 1.107*10$^{-7}$ | 5.46% | 8/triangle | 13.9% | 168.5 |
| 2 | 12/triangle | 9.016*10$^{-8}$ | 4.44% | 8/triangle | 13.9% | 171.6 |
| 3 | 12*9.2/triangle | 1.107*10$^{-7}$ | 5.46% | 8/triangle | 13.9% | 168.0 |
| 4 | 16.5/circle | 1.099*10$^{-7}$ | 5.42% | 8/triangle | 13.9% | 167.0 |

Table 1 shows four different configurations of the pillars 4 disposed in the passages 18 in the first zone of a microstructured passage module of the present invention and their corresponding spray velocities. The configuration of such microstructured passage module also includes a plurality of tunnels 17 formed by parallel rows of protrusions 5. The term "Width of Channel" in the following description represents the shortest distance between any two adjacent pillars 4 in the passages 18. The effects of pillar configuration and arrangement on spray velocity in the second zone are not discussed here. The spray velocity is measured by Computational Fluid Dynamics (CFD) software.

In a preferred embodiment of the present invention, the optimal pillar density in the passages is about 5.46% and the desired spray velocity is between 167 to 170 m/s.

We compare the No. 1 nozzle (hereinafter "No. 1") with the No. 2 nozzle (hereinafter "No. 2"). According to Table 1, the differences between No. 1 and No. 2 are the width of channel 16, and total surface area the pillars 4 occupy in the passages 18. Specifically, the width of channel 16 in No. 2 is greater than that in No. 1, but the total surface area of pillars 4 in the passages in No. 2 is less than in No. 1. The table shows that the spray velocity of No. 1 is lower than No. 2, which is consistent with the present disclosure.

We further compare No. 2 with the No. 3 nozzle (hereinafter "No. 3"). The differences between No. 2 and No. 3 are the width of channel 16, and the total surface area occupied by pillars in the passage. Note that No. 3 includes two different channel widths, which are about 12 um and about 9.2 um. According to Table 1, the total area that the pillars occupied in the passages 18 in No. 3 is greater than that of No. 2, results in higher pillar density. As a result, the spray velocity in No. 3 is lower than No. 2, which is consistent with the present disclosure.

We now turn to No. 1 and No. 3. The difference is that No. 3 has two different channel widths. However, the resulting liquid spray velocities are similar (168.5 m/s and 168.0 m/s). Accordingly, having different channel widths in first zone do not affect the spray velocity as long as the total surface area and the shape of the pillars 4 are the same. In other words, maintaining proper pillar density creates proper spray efficiency, which is consistent with spirit of the present disclosure.

We further compared No. 3 and the No. 4 nozzle (hereinafter "No. 4"). The cross-section of the plurality of pillars in the No. 4 is a circle. According to Table 1, No. 4 has the largest channel width, and the total number of pillars in the No. 4 is significantly less than that in No. 1, No. 2 or No. 3. However, the total surface area that the pillars occupied in the passages in No. 4 is similar to such in No. 1 and No. 3. Thus, the pillar density of No. 4 is similar to that of No. 1 and No. 3. The resulting spray efficiency (i.e., spray velocity) of No. 4 is similar to such in No. 1 and No. 3. Such results demonstrate that spray velocity is related to the pillar density in first zone, which supports the teaching of the present disclosure. And the width of the channel may not be a controlling factor for spray velocity.

LISTING OF ELEMENTS

Passage module 1
Central block 2
Spacer 3
Pillar 4
Protrusion 5
Plate 10
Entrance 102
Exit 104
Inclined wall 106
Sidewall 108 Aisle 15
Channel 16
Tunnel 17
Passage 18
Liquid medicament 50, 912
Protrusion column 52
Wall 54
Aerosolizer 90
Housing 902
Pump chamber 904

TABLE 2

| No. | Width of Channel In First Zone (um)/Pillar shape in the Passage/ tunnel or wall | Width of Channel Zone1 (um) | Total Surface Area Occupied by Pillars in the Passages (m$^2$) | Pillar Density (Passages) | Width of Channel Zone2/pillar shape (um) | Pillar Density (second zone) | Spray Velocity (m/s) |
|---|---|---|---|---|---|---|---|
| 5 | 16.5/Circle//wall | 16.5 | 1.107*10$^{-7}$ | 5.46 | 8(triangle) | 13.9% | 171.3 |
| 6 | 15/Circle/wall | 15 | 1.14*10$^{-7}$ | 5.6 | 15(circle) | 14% | 177.4 |
| 7 | 15/Circle/tunnel | 15 | 1.14*10$^{-7}$ | 5.6 | 15(circle) | 14% | 176 |
| 8 | 16.5/Circle/wall | 16.5 | 1.107*10$^{-7}$ | 5.46 | 8(circle) | 27.12% | 169 |

Table 2 illustrate other configurations of the present invention and their effects on spray velocity. Specifically, the data compares microstructured passage modules having the solid wall 54 configuration with the protrusions 5/tunnels 17 configuration. Here, nozzles No. 5 to 8 all have circular pillars. No. 5, 6 and 8 have a wall 54 type configuration, while No. 7 has a rows of protrusions 5 separated by tunnels 17 configuration.

Looking in conjunction with Table 1 and specifically at No. 4 and No. 5, the spray velocity for No. 5 is higher than No. 4, while the other data remain relatively similar. The marked difference between No. 4 and No. 5 is that No. 4 has tunnels, while No. 5 has a solid wall 54 arrangement. The result demonstrates that the presence of tunnels 17 may enhance aerosolization by lowering the spray velocity. This is consistent with the teaching of the present invention since tunnels allow some amount of liquid to flow traversely across passages, thereby increase flow resistance and reduce flow speed.

Data for No. 6 and No. 7 further support that the presence of tunnels 17 may lower the spray velocity and provide a desired aerosol duration.

Data for No. 5 and No. 8 support that proper pillar density in the second zone may also achieve desired spray velocity. While all other factors remain the same, increasing pillar density in No. 8 helps achieve a more desired spray velocity of 169 m/s.

No. 6 and No. 8 share almost identical configurations, except that the width of channel in the second zone for No. 6 is greater than that for No. 8 (15 um vs 8 um). The resulting spray velocity suggests that the shortest distance between two adjacent pillars in the second zone, i.e., the width of channel, is preferably about 8 um.

Spring chamber 906
Biasing element 9062
Spring 9062
Storage container 908
Tube 910
Transfusion apparatus 950
Liquid flow direction A-A'
Boundary line B

What is claimed is:

1. A microstructured passage module for an aerosol generator, comprising:
   an entrance for a liquid and an exit, wherein a direction perpendicular to the entrance defines a liquid flow direction; and
   a plate including a first zone and a second zone between the entrance and the exit, wherein the first zone comprises:
   a plurality of protrusions arranged in linear rows in the liquid flow direction, and in parallel columns over an entire width of the first zone defining a plurality of passages therebetween, the parallel columns being formed from the linear rows of the plurality of protrusions with the plurality of passages each of which having an equal width along an entire length of each passage, wherein the plurality of parallel passages corresponds to the liquid flow direction and the rows of protrusions are spaced by tunnels; and
   a plurality of pillars disposed in the second zone and in at least a section of the passages in the first zone, defining a plurality of channels inbetween, wherein a density of the plurality of pillars in the second zone is greater than that in the passages, wherein the plurality of pillars disposed in the passages increase a flow resistance for the liquid flowing through the passages, and the plurality of pillars in the section of the passages changes a flow speed for the liquid flowing through the passages, and wherein the plurality of protrusions and pillars project from and are integral parts of the plate.

2. The microstructured passage module according to claim 1, wherein the liquid flows through the plurality of passages via the tunnels.

3. The microstructured passage module according to claim 1, wherein each tunnel's length is greater than its width, and each tunnel's length is equal to each protrusion's length or width.

4. The microstructured passage module according to claim 1, wherein the tunnels have different widths.

5. The microstructured passage module according to claim 1, wherein the tunnels have same width.

6. The microstructured passage module according to claim 1, wherein a space between the pillar and the protrusion in the first zone is also part of the channel.

7. The microstructured passage module according to claim 1, wherein the plurality of pillars are arranged in a matrix-like fashion.

8. The microstructured passage module according to claim 1, wherein the plurality of pillars are arranged in a hexagonal shape.

9. The microstructured passage module according to claim 1, wherein a spray velocity is between 167 to 170 m/s.

10. The microstructured passage module according to claim 1, wherein a ratio between a total surface area that the plurality of pillars occupy in the passages to a total surface area of the passages is between 5 to 6%.

11. The microstructured passage module according to claim 10, wherein the ratio is about 5.5%.

12. The microstructured passage module according to claim 1, wherein a shortest distance between any two adjacent pillars is greater than 1 um.

13. The microstructured passage module according to claim 1, wherein the plate comprises two sidewalls in the second zone inclining towards the exit.

14. The microstructured passage module according to claim 1, wherein the plurality of pillars are further adapted to adjust a speed of the liquid flowing across the plate.

15. The microstructured passage module according to claim 1, wherein the columns of the protrusions are parallel.

16. The microstructured passage module according to claim 1, wherein the shortest distance between two adjacent pillars in the second zone is at least 8 um.

17. The microstructured passage module for an aerosol generator according to claim 1, further comprising:

a plurality of spacers arranged in rows in the liquid flow direction before the plurality of pillars and in parallel columns over an entire width of the first zone, a distance between each of the plurality of spacers being defined to be two times a width of each of the plurality of passages.

* * * * *